United States Patent [19]

Auchinleck et al.

[11] Patent Number: 5,010,900
[45] Date of Patent: Apr. 30, 1991

[54] LOWER LIMB POSITIONING APPARATUS AND SURGICAL DRAPE

[76] Inventors: Geoffrey F. Auchinleck, #5-1182 West 7th Avenue, Vancouver, British Columbia, Canada, V6H 1B4; James A. McEwen, 5259 Turquoise Drive, Richmond, British Columbia, Canada, V7C 4Z6; John C. Osborne, 4040 Toronto Street, Port Coquitlam, British Columbia, Canada, V3B 6X8; Carlo R. Bussani, 4877 Colbrook Court, Burnaby, British Columbia, Switzerland, V5G 3Y4

[21] Appl. No.: 316,852

[22] Filed: Feb. 27, 1989

[51] Int. Cl.⁵ .............................................. A61F 5/04
[52] U.S. Cl. .................................. 128/855; 206/438; 128/856
[58] Field of Search .................... 128/849, 854–856; 206/458

[56] References Cited

U.S. PATENT DOCUMENTS

| | | | |
|---|---|---|---|
| 3,968,792 | 7/1976 | Small | 128/855 |
| 4,043,328 | 8/1977 | Cawood, Jr. et al. | 128/132 D |
| 4,069,913 | 1/1978 | Harrigan | 206/278 |
| 4,153,054 | 5/1979 | Boone | 128/856 |
| 4,275,812 | 6/1981 | Poncy et al. | 128/856 X |
| 4,275,812 | 1/1981 | Poncy et al. | 206/278 |
| 4,593,699 | 6/1986 | Poncy et al. | 128/660 |
| 4,679,552 | 7/1987 | Caspari | 128/132 |
| 4,817,592 | 4/1989 | Auchinleck et. al. | 128/855 |
| 4,926,851 | 5/1990 | Bulley | 128/856 X |

*Primary Examiner*—Francis Jaworski
*Attorney, Agent, or Firm*—Klarquist, Sparkman, Campbell, Leigh & Whinston

[57] ABSTRACT

Apparatus useful in surgery for holding a patient's lower limb in a number of different positions required by a surgeon for the performance of a surgical procedure, and for eastablishing a sterile barrier between a surgical site and a patient's lower limb while the limb is being grasped by such positioning apparatus.

4 Claims, 8 Drawing Sheets

LOWER LIMB POSITIONING APPARATUS AND SURGICAL DRAPE

REFERENCE TO RELATED APPLICATIONS

This is a continuation-in-part of U.S. Ser. No. 006,131 filed Jan. 23, 1987, now U.S. Pat. No. 4,807,618, and a continuation-in-part of U.S. application Ser. No. 07/137,252, now U.S. Pat. No. 4,817,592.

FIELD OF THE INVENTION

This invention pertains to apparatus for holding a patient's lower limb in a number of different positions required by the surgeon for the performance of a surgical procedure, and pertains to related means for economically and efficiently providing a sterile barrier between the surgical site and the positioning apparatus. In particular the invention pertains to a lower limb positioning apparatus comprising a plurality of positioning members interconnecting a grasping means for grasping a part of a patient's lower limb to a supporting point, each member including selectably positionable joints which may be locked in a selected position, and apparatus for establishing a sterile barrier between a surgical site and a patient's limb, while the limb is connected to a supporting point by a limb positioning apparatus, such that the combination of the limb, limb positioning apparatus, the supporting point and the patient's body form an annular shape.

BACKGROUND OF THE INVENTION

Many surgical procedures require that a patient's lower limb or limbs be positioned in a number of different positions for the performance of the surgical procedure. It is desirable that the operating surgeon or surgical assistant be able to move the limb into other positions and configurations that may be required during the course of the surgical procedure. It is also desirable that any positioning apparatus that may be used to achieve such positions and configurations not obstruct the surgical site, and be able to avoid any obstacles that may exist around the surgical site, such as medical imaging systems, operating room lights, instrument trays, or other apparatus.

Various methods for positioning and supporting a patient's lower limb or body part are known in the prior art. One common method for positioning a body part is to have a sterile surgical assistant hold the body part in a desired position, and change the position when and as requested by the operating surgeon. This task is fatiguing for the surgical assistant, and this technique may not support the patient's body part in a sufficiently precise and rigid manner for the surgical procedure. Other typical methods for positioning a patient's limb are to rest the limb on a table for that purpose, to hang the limb over part of the operating room table, or to rest the limb on the lap of a seated operating surgeon. All of these techniques offer a very limited range of possible limb configurations, serve to restrict the movement of the surgeon, and result in reduced precision and rigidity of support.

In addition to the methods for positioning illustrated above, apparatus for supporting and positioning body parts exists in the art. One common supporting means consists of slings attached to the patient's limb, ropes and occasionally weights, which are hung over or tied to operating room light fixtures, intravenous fluid support stands, or other operating room fixtures in order to suspend the limb (e.g. see Herschman, Z. J., Frost, E. A. M, Goldiner, P. L.; Pulse Oximetry during Shoulder Arthroscopy, Anesthesiology, 65:565–566, 1986). These types of supporting means are difficult to set up and take down, clumsy to adjust, and often obstruct the surgical site. Furthermore, adjusting such apparatus to achieve a new position may require the assistance of a nonsterile person, in that operating room fixtures and support stands that may require re-positioning are not considered sterile, hence cannot be touched by a surgeon. This may preclude optimal positioning of the limb or body part, as the surgeon may no longer have direct control over the final position of the limb or body part.

Additional specialized positioning devices for supporting lower limbs are known in the prior art. One class of positioning device includes a wide variety of devices for holding a patient's leg in position for arthroscopic knee surgery. Such devices generally grip the patient's leg near the foot, and also at the thigh. Means are provided to allow the surgeon to move the lower leg into various configurations suitable for arthroscopic surgery, while the upper part of the leg is held in a fixed position These devices are generally not suitable for use during preparation of the limb for surgery, cannot be positioned so as to avoid obstacles near the surgical site, may obstruct the surgical site, do not offer any means for detaching the grasping means and attaching another grasping means for grasping another part of the patient's limb, and are difficult to drape to establish a sterile barrier between the surgical site and the patient's limb while it is grasped by the positioning device.

In an attempt to overcome the drawbacks of existing devices for holding retraction devices during surgery, the Elmed Company of Addison Ill. manufactures a multi-jointed mechanism, the "Elmed Retract-Robot", catalog number 15088-00 single arm instrument, which can be locked in a wide range of positions with a thumbscrew arrangement. This device, although not intended for manipulation of lower limbs could perhaps be adapted with appropriate grasping means to solve some of the problems heretofore described. However, such a device, even if configured with an appropriate grasping means, would still not be suitable for a wide range of surgical procedures, as the device does not provide a sufficiently large range of motion for many such procedures. It is conceivable that several such devices could be connected together to create a larger structure with an increased range of motion, but such a structure would be very difficult to re-position, in that each device in the structure would have to be unlocked, positioned and locked individually each time a new position is required. In addition, it is unlikely that several such devices connected together would offer sufficient strength to support a patient's lower limb, there is no convenient way for a grasping means to be detached and replaced with another grasping means for grasping a different part of the patient's lower limb, and the device is difficult to drape to establish a sterile barrier between the surgical site and the patient's limb while the limb is grasped by the positioning device, hence the device would typically be sterilized before each use, which is time consuming and costly.

Also known in the art is a similar retraction device, widely known by surgeons throughout the world as a "Greenberg" brain retractor. This retraction device consists of a plurality of ball and socket joints, threaded upon a length of cable. This cable may be tightened with a lever mechanism to increase the friction between each ball and socket joint. The Greenberg brain retractor is not suitable for manipulation of limbs due to its typically small size. In addition, the strength of the ball and socket joints when fully locked is insufficient to support the loads typically expected when positioning a patient's limb, there is no convenient way for a grasping means to be detached and replaced with another grasping means for grasping a different body part, and the device is difficult to drape to establish a sterile barrier between the surgical site and the patient's limb while the limb is grasped by the positioning device, hence the device would typically be sterilized before each use, which is time consuming and costly.

One problem that is common to any means of supporting a patient's limb is that of establishing a suitable sterile barrier between a surgical site and a patient's limb while it is being supported by a positioning means. The patient's limb, the positioning means, the supporting point to which the positioning means is connected, and the patient's body form a closed annular shape. This closed annular shape is usually established when the patient's limb is connected to the positioning means to hold the limb in position for preparation of the surgical site. It is undesirable to detach the patient's limb from the positioning means to apply a sterile surgical drape to the limb or positioning means after the surgical site is prepared, as this may contaminate the prepared surgical site. It is also undesirable to cover the limb and positioning means with sterile drapes before the surgical site is prepared, as the solutions used for preparation may contaminate the drape. It may be desirable, however, to be able to detach the patient's limb from the limb positioning apparatus during the surgical procedure, without compromising the sterility of the surgeon, the surgical site, or the draping material.

One method of draping such an annular shape is to drape flat sterile sheets over the limb and positioning means, and fasten the drapes in position with sterile clips or tape. This may leave openings in the drape, compromising the integrity of the sterile barrier, and will usually leave a large amount of excess drape hanging from the limb and supporting means, such that it may obstruct the surgical site.

A preferred form of sterile cover for such an annular shape consists of two elongated flexible tubes, each closed at one end, made of an impervious sterile material such as a flexible thermoplastic, which are placed over the limb and positioning means, before they are connected together, to act as sterile sleeves. Connecting the patient's limb and the positioning apparatus together through the flexible tubes allows the positioning apparatus and patient's limb to be disconnected without compromising the sterility of the surgeon or the surgical site.

A sterile drape must be packaged so that there is a means by which the sterile drape can be removed from the nonsterile outer package in such a way that the sterile drape is not contaminated. This problem is generally overcome by providing an outer package which can be opened by a nonsterile person to expose the sterile drape such that a sterile person can remove the drape without contaminating it. As the edges of the outer nonsterile package are considered to be contaminated, it is important that some means be provided to keep the edges of the outer package well away from the sterile drape and the hands of the sterile person attempting to remove the drape from the package.

Although many examples of sterile drapes in the form of an elongated flexible tubes closed at one end are known in the art, none provide a means so that such sterile drapes can be connected between a patient's limb and a limb positioning apparatus before the outer nonsterile cover is removed, and such that the non-sterile cover can be later removed without the patient's limb and the limb positioning apparatus having to be disconnected.

The following U.S. patent application of the applicants is more or less relevant to the subject matter of the applicants, invention.

U.S. application filed Feb. 19, 1986, continuation-in-part, Ser. No. 831,001; Title Advanced Medical Robot; Inventors: James Allen McEwen et.al.

SUMMARY OF THE INVENTION

The present invention provides apparatus for holding a patient's lower limb in a number of different positions required by the surgeon for the performance of a surgical procedure, said positioning apparatus consisting of a grasping means, for grasping a part of a patient's lower limb, and a plurality of positioning members connected to a supporting point, each positioning member having selectably positionable joints attached to attaching means for connecting each positioning member to other such members, or to the grasping means or to the supporting point. Each positioning member also includes a locking means for locking the joints in a selected position, an actuating means for locking and unlocking the locking means in response to a control signal, and a signal generating means which may be attached to the positioning member, so that an operator can generate control signals for locking and unlocking either individual positioning members, or predefined groups of positioning members simultaneously.

In another aspect, the invention provides apparatus for establishing a sterile barrier between a sterile surgical site and a patient's limb, while said limb is attached to a supporting point by a limb positioning apparatus, such that the combination of the limb, the limb positioning apparatus, the supporting point and the patient's body for an annular shape, and further provides means whereby the patient's limb can be disconnected from the limb positioning apparatus without subjecting the sterile barrier, surgeon or surgical site to the risk of contamination.

Another object of the invention is to provide a limb positioning apparatus consisting of a plurality of positioning members, in which said positioning members may be re-positioned individually or in groups without having an effect upon the rest of the members making up the apparatus.

Other objects of the present invention include providing a mechanism for attaching and detaching a wide variety of grasping means to the lower limb positioning apparatus, and providing a positioning apparatus that may be largely constructed out of X-ray translucent materials so that the positioning members will minimally interfere with medical X-ray images taken of the lower limb while it is held by the limb positioning apparatus.

A limb positioning apparatus in accordance with the invention comprises one or more similar positioning members, each positioning member having a cylindrical shape, at each end of which is located a ball joint mechanism providing three mutually perpendicular rotational degrees of freedom to the limb positioning apparatus. Within each positioning member is included means for alternately locking and unlocking said ball joints.

A sterile draping means in accordance with the invention consists of two elongated tubes, each closed at one end, made of a flexible, impervious sterile material, such as a flexible thermoplastic material. These elongated tubes are folded into a shape that allows one of the tubes to be inserted inside the other. The interconnected tubes are sealed within a removable impervious material which serves to protect the sterile materials from contamination, and provides a means for exposing the sterile elongated tubes without contaminating them. The draping apparatus can be placed around a positioning apparatus before it is attached to a patient's limb, and the removable impervious material removed when appropriate, to allow the sterile elongated tubes to be unrolled or unfolded over the positioning apparatus and patient's limb to establish a sterile barrier.

DETAILED DESCRIPTION OF THE PREFERRED EMBODIMENT

Figure 1:
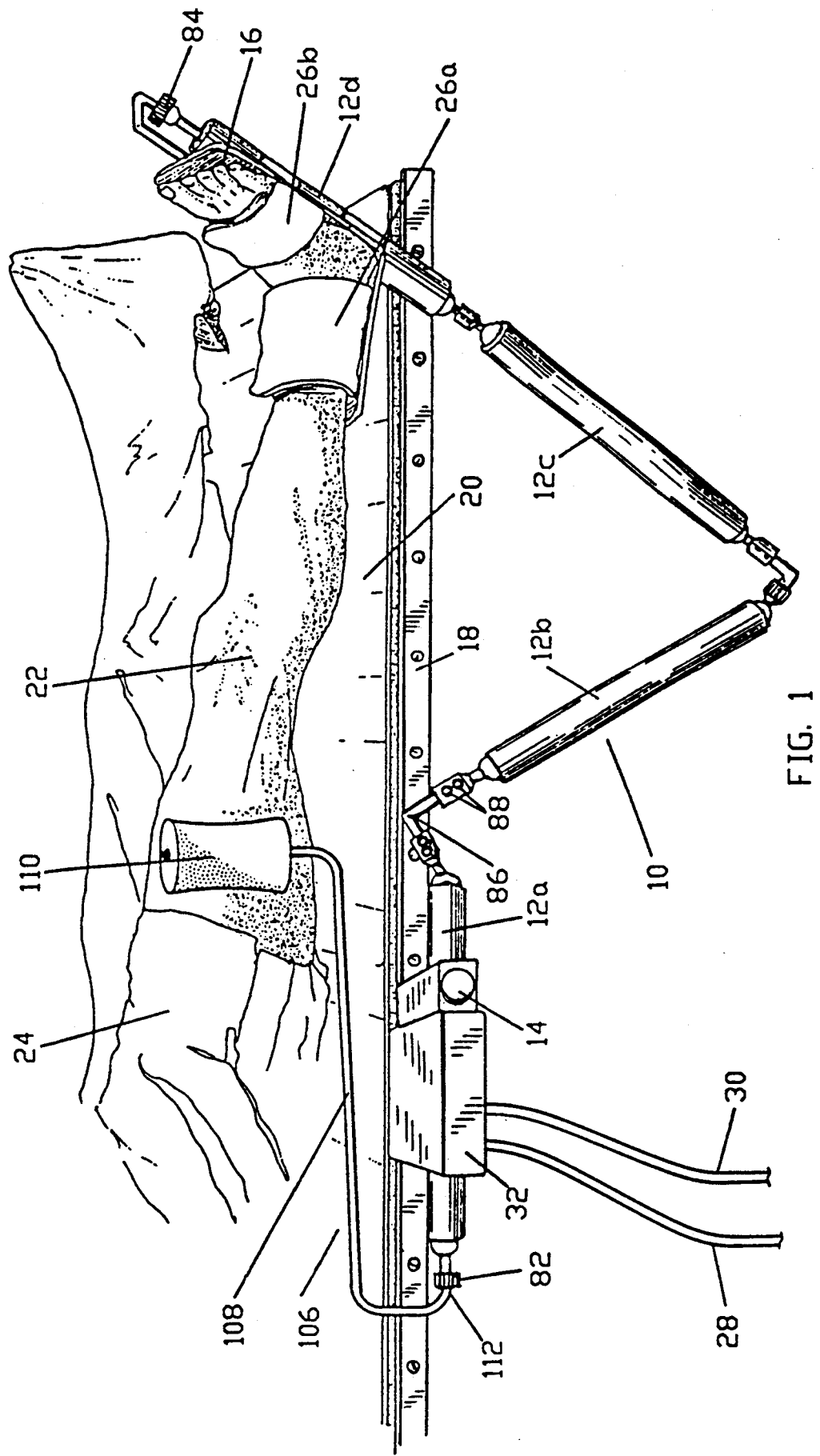
FIG. 1 is a pictorial illustration of a limb positioning apparatus configured as an leg positioner for assisting in the performance of surgical operations.

FIG. 1 is a pictorial illustration of one possible configuration of limb manipulator 10 according to the invention, as it would be used for supporting a patient's limb for arthroscopic surgery of the knee. In this configuration, limb manipulator 10 constitutes four positioning members 12a, 12b, 12c and 12d, which are connected together, and in turn are connected to table mounting means 14 and grasping means 16. Table mounting means 14 is clamped to side rail 18 of operating-room table 20, so that limb manipulator 10 will move in the same patient's entire body is re-positioned by adjusting the height, tilt or orientation of the operating-room table. Grasping means 16 is connected to limb 22 of patient 24 with fastening means 26a and 26b. Pressurized gas supply hose 28 and electrical power cord 30 are connected to electronics box 2, which is in turn attached to table mounting means 14.

Figure 2:
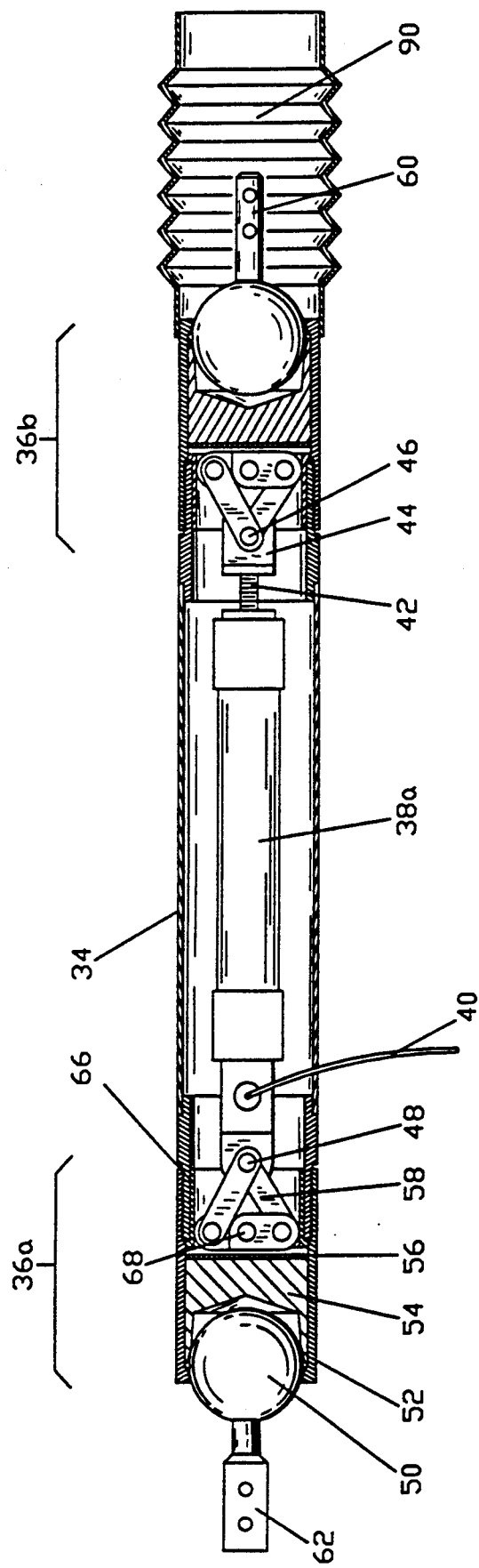
FIG. 2 is a cross section drawing of a representative positioning member of the limb positioning apparatus of FIG. 1.

A typical positioning member 12a (best seen in FIG. 2) consists of tube 34, at the ends of which are attached ball joint mechanisms 36a and 36b. Within tube 34 is pneumatic actuator 38a, which in the preferred embodiment is a Bridgestone rubber actuator (Bridgestone Corp., Tokyo, Japan). Connected to pneumatic actuator 38a is gas supply tube 40. One end of pneumatic actuator 38a is connected to a tension adjusting mechanism consisting of screw 42 and coupling 44. Coupling 44 is pivotally connected to one ball joint mechanism 36b via pivot 46. The opposite end of pneumatic actuator 38a is pivotally connected to the other ball joint mechanism 36a via pivot 48.

A typical ball joint mechanism 36a consists of ball 50, ring 52, piston cup 54, pressure plate 56, and lever mechanism 58. Ball 50 is rigidly attached to either a positioning member connection means which may consist of either stud 60 or socket 62, or accessory connection means 64 which is described below. Ball 50 is located within ring 52, which in turn is rigidly attached to tube 34. Also within ring 52 is located piston cup 54, which is free to move along the axis of tube 34 and ring 52 such that piston cup 54 can contact ball 50. Located between the flat side of piston cup 54 and lever mechanism 58 is pressure plate 56, which is preferably made of a hard material such as spring steel. Lever mechanism 58 is pivotally attached to retainer 66 with fixed pivot 68. In the preferred embodiment, lever mechanism 58 consists of four pieces of a hard material such as tool steel pivotally connected in two places to form a scissor mechanism.

In the preferred embodiment, tube 34, ring 52, piston cup 54 and retainer 66 are constructed of aluminum This material is chosen because it is translucent to X-ray imaging devices, and hence will not obscure images taken through the limb manipulator. Actuator 38a is transparent to X-ray imaging devices, such that only ball 50, pressure plate 56, lever mechanism 58, screw 42 and coupling 44 will obstruct an x-ray image. The size and location of these components is such that they will minimally obscure an X-ray image.

In operation, the condition of ball joint mechanisms 36a and 36b depend on the condition of pneumatic actuator 38a. As pressurized gas is supplied to pneumatic actuator 38a through gas supply tube 40, pneumatic actuator 38a begins to contract. This contraction force acts on lever mechanism 58, causing lever mechanism 58 to push on pressure plate 56. Pressure plate 56 pushes upon piston cup 54, causing piston cup 54 to move into contact with ball 50. Ball 50 is therefore pressed firmly into ring 52. The force of contact between ring 52 and ball 50, and piston cup 54 and ball 50, causes an increase in friction forces between these surfaces. This friction force locks ball 50 in position with respect to ring 52 and piston cup 54, preventing rotation of ball 50 about any axis. Ring 52 and piston cup 54 preferably have surfaces that are contoured to fit ball 50 to increase the friction forces and reduce the pressure between these components.

Figure 4:
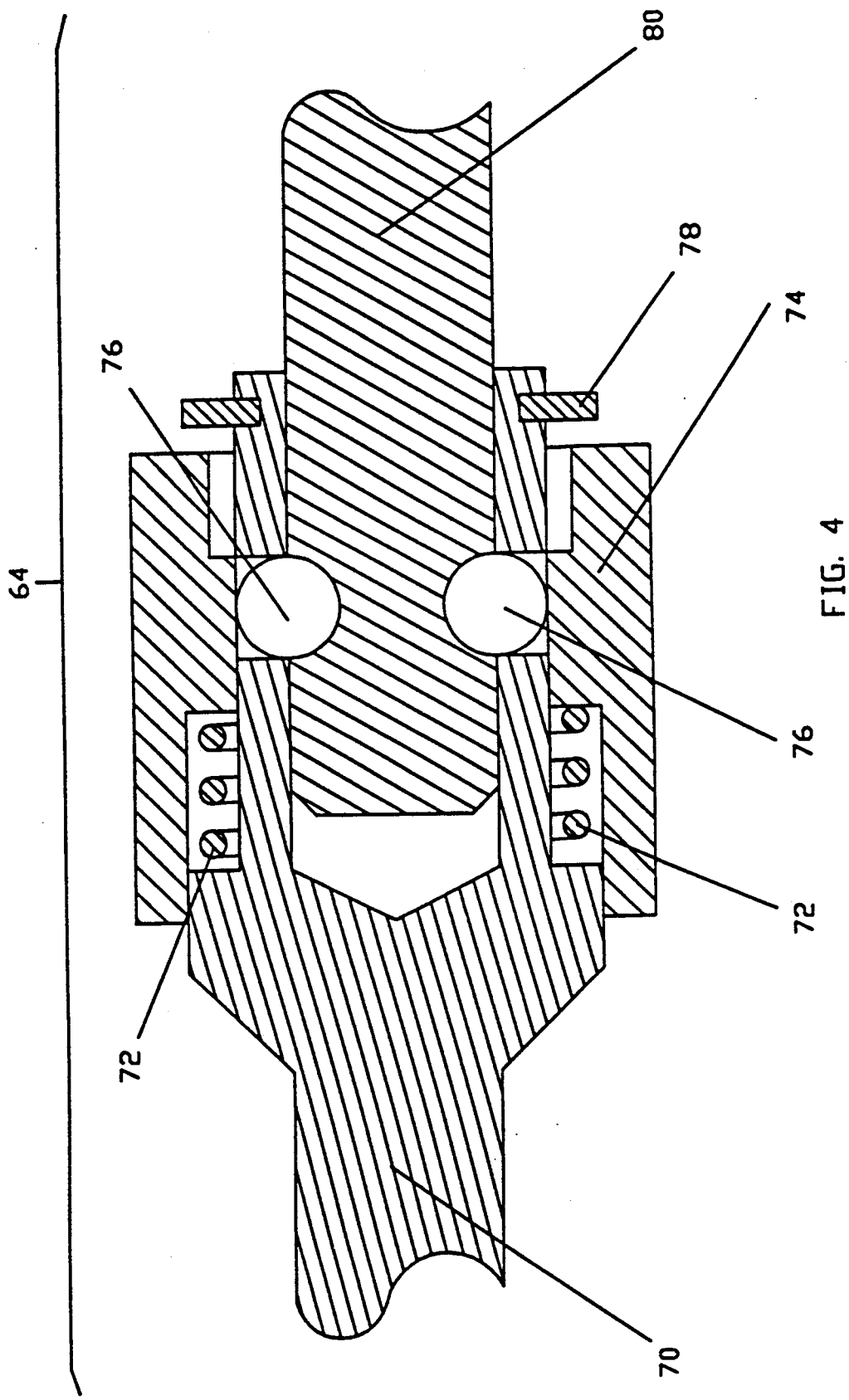
FIG. 4 is a cross section view of the accessory connection means of the limb positioning apparatus of FIG. 1.

In the preferred embodiment, positioning members 12a and 12d each have at one end, an accessory connecting means similar to accessory connecting means 64, best seen in FIG. 4. The accessory connecting means consists of socket 70, spring 72, ring 74, balls 76 and clip 78. Accessory stud 80 is constructed with dimples which align with balls 76 when accessory stud 80 is inserted in socket 70. When fully inserted, balls 76 can fall partly into the dimples in accessory stud 80, allowing spring 72 to push ring 74 over balls 76. Clip 78 prevents ring 74 from sliding off the end of socket 70. In use, a stud similar to accessory stud 80 is attached to the accessory that the user wishes to attach to the end of module 12a or 12d. To attach the accessory, the user pulls ring 74 back, and inserts the accessory stud into socket 70. When the dimples on the accessory stud are aligned with balls 76, ring 74 will move forward, locking the accessory stud into socket 70.

In the preferred embodiment, positioning members 12a and 12d are slightly different from modules 12b and 12c. Positioning member 12a is as described above, having at one end proximal accessory connecting means 82, which is similar to accessory connecting means 64 described above, and having at the other end socket 62. Modules 12b and 12c are the same as module 12a except that both ends of each module are fitted with sockets similar to socket 62. Module 12d is similar to module 12a, having at one end distal accessory connecting means 84, but having at the other end a stud similar to stud 60. Module 12a is connected to module 12b with joining piece 86 (best seen in FIG. 1). Joining piece 86 consists of two studs, similar to stud 60, welded together at an angle of approximately 90 degrees. One stud is inserted into socket 62 on the distal end of module 12a, and is held in place with two locking pins 88. Locking pins in the preferred embodiment consist of 3/16 inch diameter steel roll pins. The other stud is inserted into the socket similar to socket 62 on the proximal end of module 12b, and is held in place with two locking pins 88. Module 12c is connected to module 12b with a second joining piece similar to joining piece 86. Module 12d is connected to the distal end of module 12c by inserting the stud similar to stud 60 of module 12d into the socket similar to socket 62 on the distal end of module 12c and locking the stud in place with two locking pins 88. A protective sleeve similar to sleeve 90 (not shown in FIG. 1), which in the preferred embodiment consists of a short section of plastic bellows, is fitted between each pair of positioning members.

Figure 3:
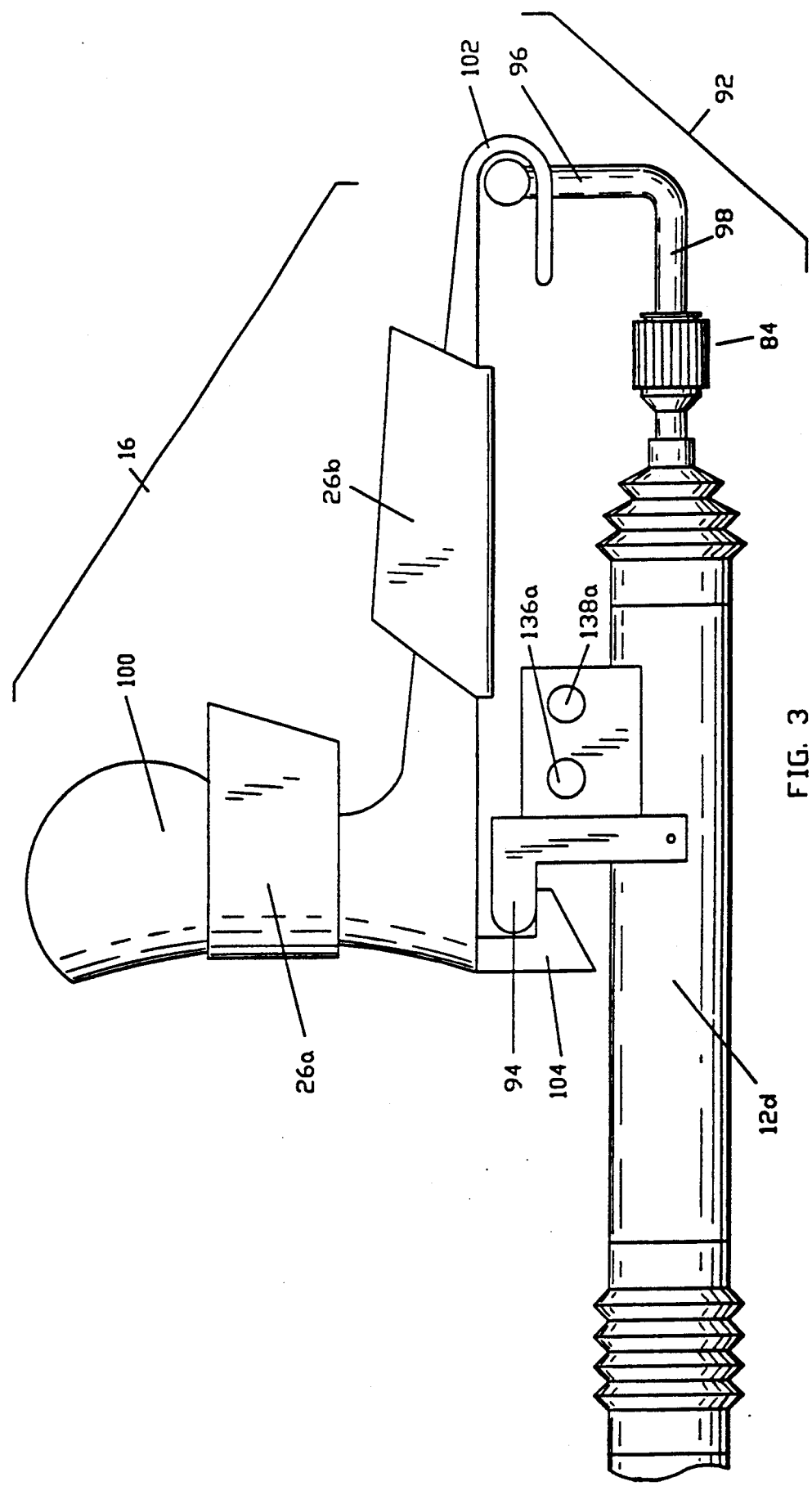
FIG. 3 is a side elevation view of the grasping means of the limb positioning apparatus of FIG. 1.

Limb manipulator 10, consisting of positioning members 12a, 12b, 12c and 12d connected together, may be connected to grasping means 16 via distal accessory connecting means 84, using coupler 92 and spring clip 94 (best seen in FIG. 3). Coupler 92 consists of 'T' piece 96 and stud 98, which is similar to accessory connecting stud 80. Grasping means 16 consists of rigid cast plastic foot restraint 100 to which is fastened hook 102, which mates with 'T' piece 96. Also attached to foot restraint 100 is catch 104. Catch 104 fits into spring clip 94, which is attached to module 12d. Attached to foot restraint 100 are fastening means 26a and 26b, which in the preferred embodiment consist of two Velcro TM straps. In use, fastening means 26a and 26b are used to rigidly attach patient's limb 22 to grasping means 16.

Thigh supporting means 106, which is best seen in FIG. 1, may be connected to limb manipulator 10 via proximal accessory connection means 82. Thigh supporting means 106 consists of arm 108 and padded post 110. Arm 108 is, in the preferred embodiment, made of a section of stainless steel shaft, bent so as to form a hooked shape. Padded post 110 is attached perpendicular to arm 108, at the distal end of arm 108. At the proximal end of arm 108 is attached accessory connecting stud 112, which is similar to accessory connecting stud 80 described above.

The grasping means shown is FIG. 3 is only one of many possible grasping means that could be used with limb manipulator 10. Grasping means suitable for grasping an upper leg, ankle or other limb portion could be connected to limb manipulator 10 in place of grasping means 16 by disconnecting coupler 92 from distal accessory connection means 84 and connecting a different grasping means.

Similarly, the thigh supporting means shown in FIG. 1 is only one a large number of possible supporting arms or members that could be attached to proximal accessory connection means 82. Various other supporting means could be attached to proximal accessory connection means 82, including, for example, a means for attaching to a tourniquet cuff in order to tightly grasp the upper portion of the patient's leg, a support post intended to fit into the patient's groin to act as a counter traction support for surgical procedures requiring traction on the lower limbs, or other accessories for measuring and recording lateral or longitudinal forces on the patient's leg.

Figure 5:
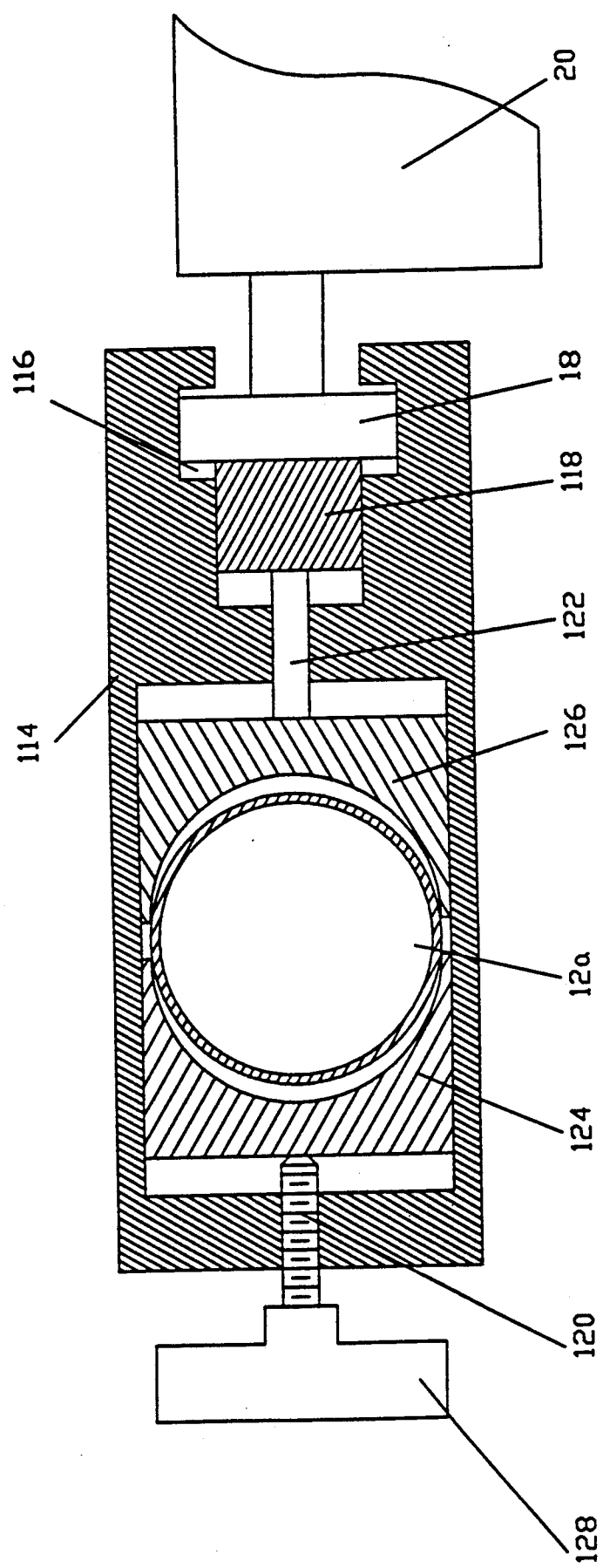
FIG. 5 is a cross section side elevation view of the table mounting means of the limb positioning apparatus of FIG. 1.

Limb manipulator 10 consisting of interconnected positioning members 12a, 12b, 12c and 12d may be attached to operating-room table side rail 18 via table mounting means 14 (best seen in FIG. 5). Table mounting means 14 consists of mounting block 114, in which is cut channel 116 constructed to fit over side rail 18 of operating-room table 20. Mounting block 114 is fitted around module 12a so as to allow mounting block to rotate about the long axis of module 12a. Moveably attached to mounting block 114 is pressure bar 118, which is free to move laterally within channel 116. Within mounting block 114 are threaded rod 120, pin 122, and clamping pads 124 and 126. Threaded rod 120 can come in contact with clamping pad 124, which in turn presses against proximal module 12a. Proximal module 12a in turn presses against clamping pad 126, which in turn presses upon pin 122, which presses upon pressure bar 118.

In use, mounting block 114 is rotated about the axis of module 12a so as to position channel 116 on the correct side of module 12a such that it will be aligned with the table side rail 18 of operating room table 20. Channel 116 is positioned over table side rail 18 such that table side rail 18 is within channel 116. Threaded rod 120 can be rotated by the user using handle 128 to increase the pressure on clamping pad 124, which clamps proximal module 12 against clamping pad 126, which in turn presses upon pin 122 which will then come into contact with pressure bar 118. Pressure bar 118 is thus moved laterally until it is pressed against table side rail 18 to rigidly clamp table side rail 18 between mounting block 114 and pressure bar 118, while simultaneously rigidly clamping module 12a between clamping pads 124 and 126, thereby rigidly fixing table mounting means 14 to operating-room table 20 as well as rigidly fixing module 12a to mounting block 114.

Also attached to proximal module 12a is electronics box 32. Within electronics box 32 are power supply 130, valves 132a, and 132b, and control circuitry 134 (best seen in FIG. 6)

Connected to module 12d near spring clip 94 are control switches 136a, 136b, 138a and 138b (best seen in FIG. 6). control circuitry 134 via control wires 140. Control switches 136a, 136b, 138a and 138b are alternate action type switches, which must be pressed once to change position and pressed again to return to the initial state. Control switches 136a, 136b, 138a, and 138b are connected together in pairs so that pressing either of control switches 136a or 136b will cause valve 132a to activate Pressing either the same control switch a second time, or the other control switch for the first time, will de-activate valve 132a. Pressing either of control switches 138a or 138b will cause valves 132a and 132b to activate. Pressing either the same control switch a second time, or the other control switch for the first time, will de-activate valves 132a and 132b. Valve 132a, when activated cuts off the supply of pressurized gas to actuator 38a within positioning member 12a. In this way, control switches 136a and 136b control the flow of pressurized gas to only positioning member 12a, allowing the user to lock and unlock the ball joint mechanisms 36a and 36b of positioning member 12a without affecting the state of positioning members 12b, 12c, or 12d. Control switches 138a and 138b activate both of valves 132a and 132b. As the air supply lines for modules 12b, 12c, and 12d are all connected to valve 132b, it can be seen that control switches 138a and 138b control the flow of pressurized gas to all four to lock and unlock the ball joint mechanisms of all four positioning members simultaneously.

In the preferred embodiment, control switches 136a, 136b 138a and 138b are located on positioning member 12d. If such a control means is not convenient, these control switches may be replaced with other means for activating valves 132a and 132b. These other activating means may consist of footswitches, sterile hand controls, or other switching means operated by a non-sterile surgical assistant. The control switches described could also be located in convenient places other than on limb manipulator 10, such that each positioning member of limb manipulator 10 could be locked and unlocked from a remote location.

In the preferred embodiment, valves 132a and 132b are SMC NZ3245 normally open pilot operated valves (SMC Pneumatic Inc., Indianapolis Ind., U.S.A.). Normally open valves are used so that pressurized gas is delivered to actuators 38a, 38b, 38c and 38d in each positioning member 12a, 12b 12c and 12d when valves 132a and 132b are not activated, which causes the ball joint mechanisms of each positioning member 12a, 12b, 12c and 12d to lock. In this way, loss of electrical power to control circuitry 134 will not cause the ball joint mechanisms within positioning members 12a, 12b, 12c or 12d to unlock.

Pneumatic check valves 142a and 142b, which in the preferred embodiment are Clippard MCV-1 check valves (Clippard Instrument Laboratory, Inc., Cincinnati, Ohio, U.S.A.), serve a similar function in that they serve to maintain pressure in pneumatic actuators 38a, 38b, 38c and 38d within positioning members 12a, 12b, 12c and 12d in the event that gas pressure in gas supply hose 28 drops below an acceptable level.

Figure 7:
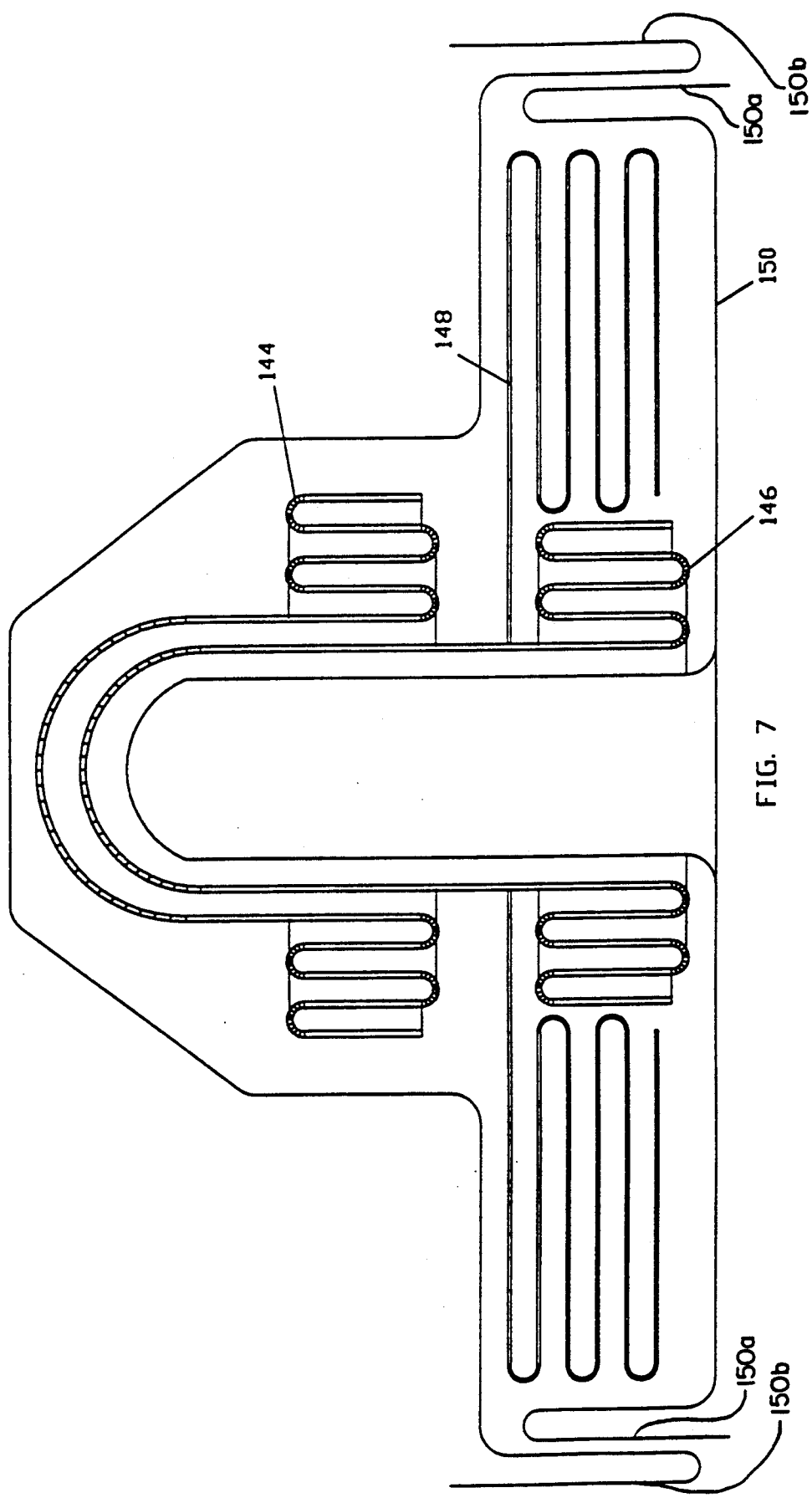
FIG. 7 is a cross section of a draping apparatus suitable for use in conjunction with the apparatus of FIG. 1.

In use, it may be desirable to establish a sterile barrier between limb manipulator 10 and the surgical site. A suitable apparatus for establishing such a sterile barrier consists of sterile elongated flexible tube 144 and sterile elongated flexible tube 146, both of which are closed at one end, and sterile fenestrated extremity sheet 148 (best seen in FIG. 7). Elongated flexible tubes 144 and 146 and fenestrated extremity sheet 148 may be constructed of a flexible thermoplastic material, fabric or non-woven material which may be sterilized. Elongated flexible tube 144 is partly rolled or folded up from the open end. The closed end of elongated flexible tube 146 is pushed through the fenestration in extremity sheet 148, and into the open end of elongated flexible tube 144. The open end of elongated flexible tube 146 is also partly rolled or folded up from the open end. Sterile outer wrap 150 is sealed around both elongated flexible tubes 144 and 146 and extremity sheet 148, and is formed in such a way that part of outer wrap 150 fits inside both elongated flexible tubes 144 and 146 and through the fenestration in extremity sheet 148. Outer wrap 150 is sealed in such a way that it may be removed during use, so that elongated tube 144 can be turned inside out and extended over grasping means 16 and patient's limb 22, extremity sheet 48 can be moved along patient's limb 22 up to the upper part of patient's limb 22 and unfolded, and elongated tube 146 can be extended over limb positioner 10, an hereinafter described.

OPERATION BY SURGICAL STAFF

As shown in FIG. 1, patient 24 is positioned on operating-room table 20 in a normal position for the surgery to be performed, and anesthetized in accordance with standard medical procedures.

Limb manipulator 10 is attached to a convenient place on operating-room table 20 by rotating mounting block 114 around module 12a so that channel 116 cut into mounting block 114 is aligned with the appropriate side of operating-room table 20. Operating-room table side rail 18 is then fitted into channel 116 cut into mounting block 114 and threaded rod 120 is turned with handle 128 until pressure bar 118 is firmly clamped against operating-room table side rail 18 and module 12a is firmly clamped between clamping pad 124 and clamping pad 126. Limb positioner 10 is then connected to an electrical supply via electrical power cord 30 and a pressurized gas supply via pressurized gas supply line 28.

Coupling means 44 is attached to distal accessory connection means 84. Grasping means 16 is attached to patient's limb 22 by tightly wrapping fastening means 26a and 26b about limb 22.

The draping apparatus is installed by fitting the distal end of limb manipulator 10 into outer wrap 150 such that the distal end of limb manipulator 10 is pushed into the open end of both elongated flexible tubes 144 and 146, and through the fenestration in extremity sheet 148. The draping apparatus is pulled over limb manipulator 10 until 'T' piece 96 is located inside the closed ends of elongated flexible tubes 144 and 146.

Limb manipulator 10 is located in an appropriate orientation for attaching grasping means 16, and patient's limb 22 to limb manipulator 10. Hook 102 is fitted over 'T' piece 96, located at the end of coupler 92, such that the various layers of the draping apparatus are located between hook 102 and 'T' piece 96. Spring clip 94 and catch 104 are not yet engaged. Patient's limb 22 is then prepared for surgery in accordance with standard operating room procedures.

When the preparation of patient's limb 22 is complete, outer wrap 150 surrounding the various components of the draping apparatus is removed. Outer wrap 150 is removed by a non-sterile person who pulls apart sealed tabs 150a and 150b. A sterile person can then pull elongated flexible tube 144 over grasping means 16, and unroll it along the patient's limb 22. Extremity sheet 148 can then be pulled over the distal end of limb manipulator 10, grasping means 16, and moved along patient's limb 22 until it is located at the proximal part of patient's limb 22. Extremity sheet 148 can then be unfolded using standard operating technique, so as to cover patient 24 and operating room table 20. Finally, elongated flexible tube 146 may be unrolled along limb manipulator 10, completing the sterile barrier.

When the sterile barrier is complete, catch 104 is pressed into spring clip 94 to rigidly attach grasping means 16 to limb positioner 10.

In use, operating surgeon 116 may desire to change the position of limb 22 or limb manipulator 10. To do this, the operating surgeon grasps positioning member 12d, and depresses either of control switches 138a or 138b, which causes valve 132b to release, which in turn causes all of the ball joint mechanisms in positioning members 12b, 12c and 12d to release. The surgeon may then move patient's limb 22 and modules 12b, 12c, and 12d into a new position. When a new desired position is reached, the operating surgeon presses either control switch 138a or control switch 138b, which deactivates the valve 132b, causing the ball joint mechanisms of positioning members 12b, 12c, and 12d to lock.

The operating surgeon may wish to change the position of thigh supporting means 106. To do this, the surgeon grasps positioning member 12d, and depressed control switch 136a or 136b, which causes valve 132a to release, which in turn causes both of the ball joint mechanisms in positioning member 12a to release. The surgeon may then move thigh supporting means 106 into a new position, and move patient's limb 22 slightly as well. When a new desired position is reached, the operating surgeon presses either control switch 136a or control switch 136b, which deactivates the valve 132a, causing the ball joint mechanisms of positioning member 12a to lock.

When the surgical procedure is complete, sterile elongated flexible tubes 144 and 146, and extremity sheet 148 are cut away and discarded and fastening means 26a and 26b are undone to release patient's limb 22 from grasping means 16. Table mounting means 14 is then removed from table side rail 18 by undoing threaded rod 120. Limb manipulator 10 is then removed to storage.

Many alterations and adaptations may be made to the preferred embodiment described herein. Accordingly, the invention is to be limited only by reference to the appended claims. For example, although the preferred embodiment herein described consists of four positioning members, more or fewer positioning members could be used for increased functional capability. Also, the pneumatic actuators used in the preferred embodiment could be replaced with other pneumatic, hydraulic, or electric actuators to achieve a similar function. The positioning apparatus could also be equipped with a variety of grasping means designed to attach to or support a wide variety of limbs or body parts. The positioning apparatus may also be used as a device for positioning a wide variety of therapeutic or diagnostic apparatus, such as retractors, arthroscopy cameras, suction catheters, mechanisms for applying traction, or other tools or apparatus which must be positioned near the surgical site.

Figure 8:
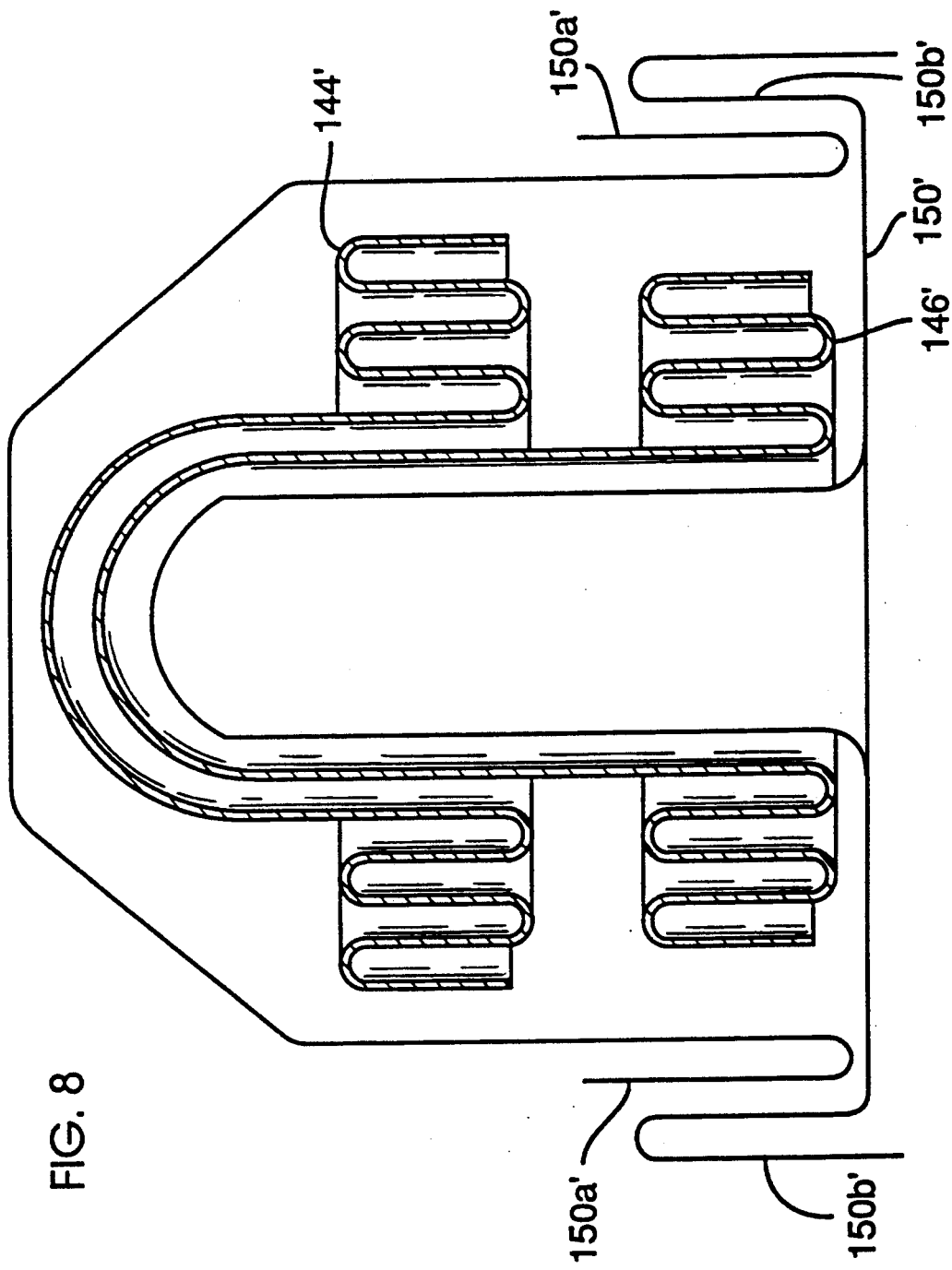
FIG. 8 is a cross section of an alternate embodiment of a draping apparatus suitable for use in conjunction with the apparatus of FIG. 1.

One alternative embodiment of the sterile draping apparatus described above is shown in FIG. 8. This embodiment is similar to the embodiment described above, except that an extremity sheet 148 is not included within outer wrap 150'. This permits the user to use a different means to drape operating room table 20 and patient 24 while preparing for surgery. In addition, outer wrap 150', which is sealed around tubes 144' and 146', can thus be made somewhat smaller than in the previously described embodiment. Outer wrap 150' is removed by a non-sterile person who pulls apart sealed tabs 150a' and 150b'.

The apparatus herein described for applying a surgical drape to patient's limb 22 and limb positioner 10 could also be used, with some modification, for a wide variety of sterile draping applications. For example, in any surgical procedure in which a limb or body part is to be supported with a structure fastened to the operating-room table or some other fixed support, the sterile draping apparatus described could be used to establish a sterile barrier between the limb or body part and the sterile surgical site. This could include a patient's leg supported by a traditional arthroscopic leg holder, a patient's arm resting upon a supporting table, or a patient's limb held in a traction apparatus.

We claim:

1. A surgical drape assembly, comprising:
   a first flexible tube having an open end and
   a second flexible tube having an open end and a closed end, the closed end of the second flexible tube being disposed within the first flexible tube; and
   removable flexible wrap material sealed around the first and second flexible tubes, the wrap material extending into the second flexible tube to define a space into which an object may be inserted to be within the second flexible tube with the wrap material positioned between the object and the second flexible tube.

2. The assembly of claim 1 further including a sheet of flexible material sealed within the wrap material, the sheet of flexible material having an opening through which the closed end of the second flexible tube extends.

3. Apparatus for forming a sterile barrier around a body part and around a positioning apparatus that supports the body part, comprising:
   (a) a first tube of sterile flexible material, closed at one end, and gathered together at the open end, such that the first elongated tube can be extended over the body part; and
   (b) a second tube of sterile flexible material, closed at one end, and gathered together at the open end, the closed end of which is inserted into the open end of the first tube, such that the second tube can be extended over the positioning apparatus; and
   (c) removable impervious material enclosing the first and second flexible tubes, and extending into the open ends of the first and second flexible tubes, such that the positioning apparatus can be inserted into the open end of both the first and second flexible tubes while the first and second flexible tubes are enclosed by the removable impervious material.

4. Apparatus for forming a sterile barrier around a body part and around a positioning apparatus that supports the body part, comprising:
   (a) a first tube of sterile flexible material, closed at one end, and gathered together at the open end, such that the first tube can be extended over the body part; and
   (b) a flat sheet of sterile flexible material within which is a hole, the edges of the sheet being gathered together, such that the flat sheet can be moved along the body part and extended to cover the area surrounding the body part; and
   (c) a second tube of sterile flexible material, closed at one end, and gathered together at the open end, the closed end of the second tube being inserted through the hole in the flat sheet and into the open end of the first tube, such that the second tube can be extended over the positioning apparatus; and
   (d) removable impervious material enclosing the first and second flexible tubes and the flat sheet, and extending into the open ends of the first and second flexible tubes and through the hole in the flat sheet, such that the positioning apparatus can be inserted into the open end of both the first and second flexible tubes and through the hole in the flat sheet while the first and second flexible tubes and the flat sheet are enclosed by the removable impervious material.

* * * * *

UNITED STATES PATENT AND TRADEMARK OFFICE
CERTIFICATE OF CORRECTION

PATENT NO. : 5,010,900

DATED : April 30, 1991

INVENTOR(S) : Geoffrey F. Auchinleck et al.

It is certified that error appears in the above-identified patent and that said Letters Patent is hereby corrected as shown below:

Cover page, delete "4,275,812 1/1981 Poncy et al 206/278".

Abstract, line 4, "eastablishing" should be --establishing--.

Column 1, line 8, "U.S. Ser. No." should be --U.S. application Ser. No.--.

Column 2, line 24, insert "." between words "position" and "These".

Column 4, line 2, "of an elongated" should be --of elongated--.

Column 4, line 12, "applicants," should be --applicants'--.

Column 4, line 14, insert ":" after the word "Title".

Column 4, line 54, insert ":" after the word "include".

Column 5, line 23, "as an" should be --as a--.

Column 5, line 55, insert "reference frame as the patient's entire body when the" between "same" and "patient's".

Column 5, line 61, "box 2" should be --box 32--.

Column 6, line 27, insert "." after the word "aluminum".

Column 8, line 2, "one a" should be --one of a--.

Figure 6:
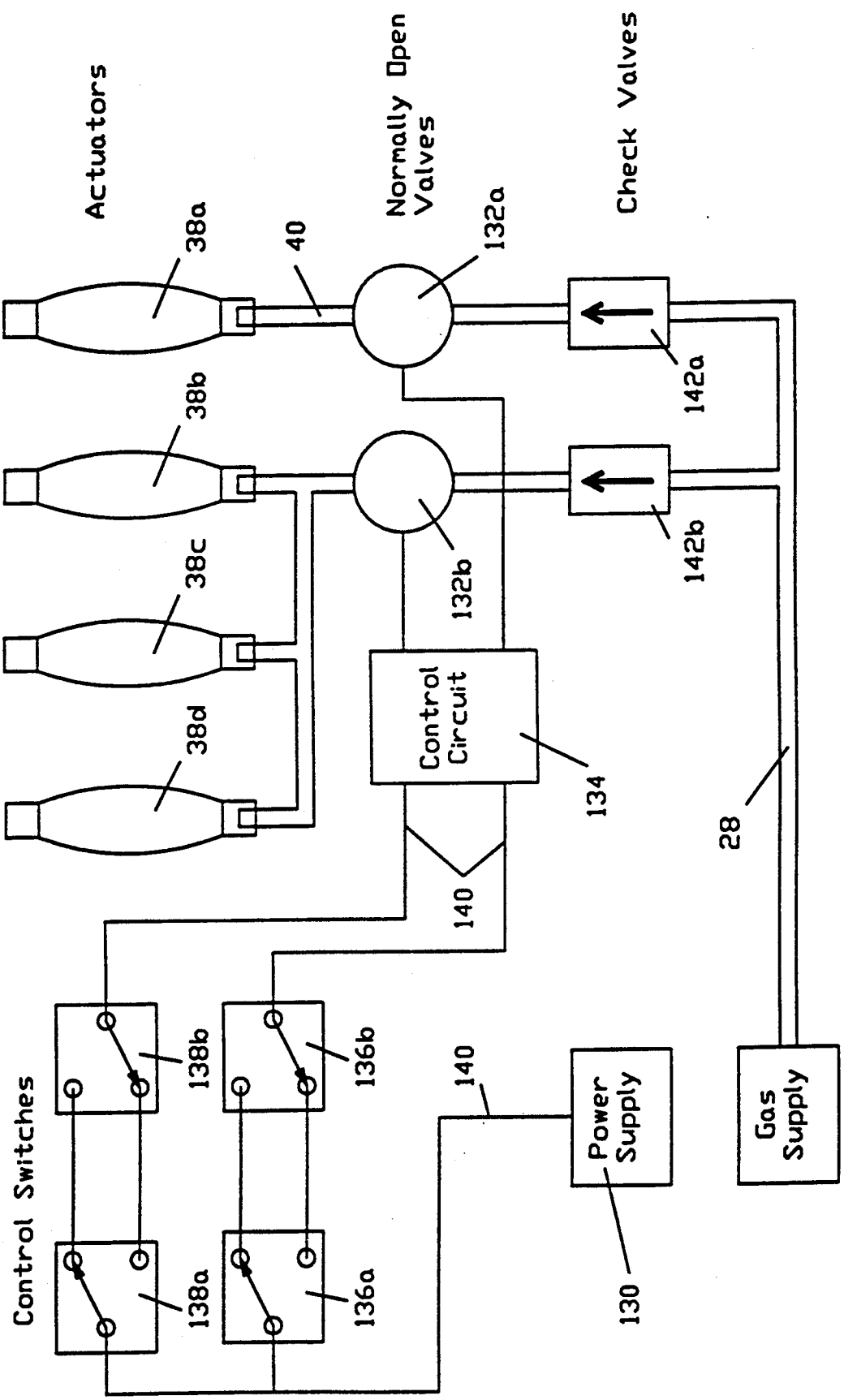
FIG. 6 is a schematic diagram of the electronic and pneumatic circuit of the apparatus of-FIG. 1.

Column 8, line 53, insert "." after "FIG. 6)".

Column 8, line 56, insert "Control switches 136a, 136b, 138a and 138b are connected to" between "FIG. 6)." and "control".

Column 8, line 63, insert "." between "activate" and "Pressing".

Column 9, line 12, insert "positioning members 12a, 12b, 12c and 12d, allowing the user" between "four" and "to".

UNITED STATES PATENT AND TRADEMARK OFFICE
CERTIFICATE OF CORRECTION

PATENT NO. : 5,010,900

Page 2 of 2

DATED : April 30, 1991

INVENTOR(S) : Geoffrey F. Auchinleck et al.

It is certified that error appears in the above-identified patent and that said Letters Patent is hereby corrected as shown below:

Column 9, line 16, insert "," between "136b" and "138a".
    Column 9, line 32, insert "," between "12b" and "12c".
    Column 10, line 3, "48" should be --148--.
    Column 10, line 6, "an" should be "and".
    Column 12, line 6, insert "a closed end;" between "and" and "a".

Signed and Sealed this

Twentieth Day of April, 1993

Attest:

MICHAEL K. KIRK

Attesting Officer

Acting Commissioner of Patents and Trademarks